United States Patent
Gu et al.

(10) Patent No.: US 11,654,378 B2
(45) Date of Patent: May 23, 2023

(54) SENNA OBTUSIFOLIA SEED EXTRACT AND A METHOD FOR COMPREHENSIVE DEVELOPMENT AND UTILIZATION OF SENNA OBTUSIFOLIA SEEDS

(71) Applicants: Sujing Gu, Luohe (CN); Ziheng Jin, Luohe (CN); Yanjun Wen, Luohe (CN); Linzheng Li, Luohe (CN)

(72) Inventors: Sujing Gu, Luohe (CN); Ziheng Jin, Luohe (CN); Yanjun Wen, Luohe (CN); Linzheng Li, Luohe (CN)

(73) Assignee: HENAN ZHONGDA HENGYUAN BIOTECHNOLOGY STOCK CO., LTD., Henan (CN)

( * ) Notice: Subject to any disclaimer, the term of this patent is extended or adjusted under 35 U.S.C. 154(b) by 147 days.

(21) Appl. No.: 17/352,295

(22) Filed: Jun. 19, 2021

(65) Prior Publication Data
US 2021/0402324 A1 Dec. 30, 2021

(30) Foreign Application Priority Data

Jun. 30, 2020 (CN) .......................... 202010616852.9

(51) Int. Cl.
| | | |
|---|---|---|
| B01D 11/02 | (2006.01) | |
| C07C 50/18 | (2006.01) | |
| C08B 37/08 | (2006.01) | |
| B01D 11/04 | (2006.01) | |
| B01D 61/14 | (2006.01) | |
| C08B 37/00 | (2006.01) | |

(52) U.S. Cl.
CPC ...... *B01D 11/0288* (2013.01); *B01D 11/0284* (2013.01); *B01D 11/0415* (2013.01); *B01D 11/0492* (2013.01); *B01D 61/145* (2013.01); *C07C 50/18* (2013.01); *C08B 37/0087* (2013.01)

(58) Field of Classification Search
CPC ............ B01D 11/0288; B01D 11/0292; B01D 11/048; B01D 11/0257; B01D 11/0296; B01D 11/0415; B01D 11/0492; B01D 21/26; B01D 21/262; B01D 36/00; B01D 36/045; B01D 37/00; B01D 61/14; B01D 61/145; B01D 2311/02; B01D 2311/2642; B01D 2311/2649; B01D 2311/2676; B01D 11/0284; C07D 311/28; A61K 36/72; A61K 31/352; A61K 2236/333; A61K 2236/51; A61K 2236/53; A61K 36/482; A61K 2236/15; A61K 2236/55; A23L 2/38; A23L 33/105; C08B 37/0087; C08B 37/0003; C07C 50/18; C07C 46/10; C07C 2603/24
See application file for complete search history.

(56) References Cited

U.S. PATENT DOCUMENTS

| | | | | |
|---|---|---|---|---|
| 3,364,113 A | * | 1/1968 | Friedmann | A61K 36/482 514/33 |
| 3,517,269 A | * | 6/1970 | Honerlagen | A61K 36/482 536/18.5 |
| 4,256,875 A | * | 3/1981 | Gabriel | A61K 36/482 536/18.1 |
| 5,574,151 A | * | 11/1996 | Toikka | A61P 1/10 536/127 |
| 2015/0259370 A1 | * | 9/2015 | Baez-Vasquez | D21H 11/12 435/212 |
| 2018/0147221 A1 | * | 5/2018 | von Maltzahn | A61K 45/06 |
| 2018/0338513 A1 | * | 11/2018 | Lian | C09B 61/00 |
| 2020/0352206 A1 | * | 11/2020 | Wagner-Salvini | A61K 36/33 |

FOREIGN PATENT DOCUMENTS

| | | | | |
|---|---|---|---|---|
| JP | h05345724 A | * | 12/1993 | ............. A61K 35/78 |
| WO | WO2014184779 A1 | * | 11/2014 | ........... A61K 36/482 |

OTHER PUBLICATIONS

Nakajima et al, English translation of patent publication JP H05345724A, published Dec. 1993. (Year: 1992).*
Harry-O'Kuru et al, "Sicklepod (*Senna obtusifolia*) Seed Processing and Potential Utilization", published in J. Agric. Food Chem, 2005, vol. 53, pp. 4784-4787. (Year: 2005).*
Harry-O'Kuru et al, "Processing Scale-Up of Sicklepod (*Senna obtusifolia* L.) Seed", published in J. Agric. Food Chem, 2009, vol. 57, pp. 2726-2731. (Year: 2009).*
Kowalczyk et al, "An Extract of Transgenic *Senna obusifolia* L. hairy roots with Overexpression of PgSS1 Gene in Combination with Chemotherapeutic Agent Induces Apoptosis in the Leukemia Cell Line", published in Biomolecules, vol. 10(4), 25 pages, published date of Apr. 2020. (Year: 2020).*

* cited by examiner

*Primary Examiner* — Joseph W Drodge

(57) ABSTRACT

A method of preparing a *Senna obtusifolia* seed extract rich in anthraquinones and a galactomannan extract includes the following steps: (1) crushing *Senna obtusifolia* seeds into a *Senna obtusifolia* seed powder; (2) extracting the *Senna obtusifolia* seed powder with 40-85% ethanol, filtering to obtain an extract solution and a residue; (3) concentrating the extract solution under vacuum to obtain a concentrated extract solution, spray-drying the concentrated extract solution to obtain the *Senna obtusifolia* seed extract; (4) extracting the residue with membrane filtered water, conducting a centrifugation to obtain a supernatant; (5) adding ammonium sulfate and ethanol to the supernatant to form a two-phase aqueous system, collecting a bottom layer of the two-phase aqueous system; and (6) conducting an ultrafiltration of the bottom layer with a cut-off molecular weight of 50 k-200 k to obtain a galactomannan extract solution, drying the galactomannan extract solution under vacuum to obtain the galactomannan extract.

10 Claims, No Drawings

SENNA OBTUSIFOLIA SEED EXTRACT AND A METHOD FOR COMPREHENSIVE DEVELOPMENT AND UTILIZATION OF SENNA OBTUSIFOLIA SEEDS

This application claims priority to Chinese Patent Application No. 202010616852.9, filed on Jun. 30, 2020, which is incorporated by reference for all purposes as if fully set forth herein.

TECHNICAL FIELD

The invention relates to herb medicine and food, in particular to a method of a *Senna obtusifolia* seed extract rich in anthraquinones and a galactomannan extract.

TECHNICAL BACKGROUND

*Senna obtusifolia* seeds are one of herb medicine and food announced by the Ministry of Health. They are the dried mature seeds of *Cassiaobtusifolia* L. or *Cassia tora* L. and can lower blood pressure and blood lipids, improve eyesight, and have antibacterial and other effects. Anthraquinones are the main medicinal ingredients of *Senna obtusifolia* seeds, mainly including chrysophanol, cassia, emodin, cassia cassia, orange cassia, etc. *Senna obtusifolia* seeds are also rich in polysaccharides, mainly galactomannan, which can be used as a thickening and emulsifying food additive.

At present, the anthraquinones, the medicinal component of *Senna obtusifolia* seeds, are mostly prepared by ethanol extraction, but there is a large amount of residue, which cause a serious waste of resources. The main component of the residue is polysaccharides, which are rich in galactomannan and can be developed as food additives. At present, the extraction and purification of *Senna obtusifolia* seed polysaccharides mostly use water extraction and alcohol precipitation, but there are still a lot of impurities, and the galactomannan purity is low or *Senna obtusifolia* seeds are classified by grinding and sieving to obtain endosperm rich in polysaccharides, and then extracted with isopropanol and purified to obtain *Senna obtusifolia* seed galactomannan. The process is complicated and product contains isopropanol residues. There is a need for a comprehensive extracting method with improved product quality.

SUMMARY OF THE INVENTION

In one embodiment, the present application provides a method of preparing a *Senna obtusifolia* seed extract rich in anthraquinones and a galactomannan extract. The method includes the following steps: (1) crushing *Senna obtusifolia* seeds into a *Senna obtusifolia* seed powder; (2) extracting the *Senna obtusifolia* seed powder with 40-85% ethanol, filtering to obtain an extract solution and a residue; (3) concentrating the extract solution under vacuum to obtain a concentrated extract solution, spray-drying the concentrated extract solution to obtain the *Senna obtusifolia* seed extract; (4) extracting the residue with membrane filtered water, conducting a centrifugation to obtain a supernatant; (5) adding ammonium sulfate and ethanol to the supernatant to form a two-phase aqueous system, collecting a bottom layer of the two-phase aqueous system; and (6) conducting an ultrafiltration of the bottom layer with a cut-off molecular weight of 50 k-200 k to obtain a galactomannan extract solution, drying the galactomannan extract solution under vacuum to obtain the galactomannan extract.

In another embodiment, in the step (1), the *Senna obtusifolia* seed powder has a particle size of 20-60 mesh.

In another embodiment, in the step (2), an amount of the 40-85% ethanol is 3-15 times of an amount of the *Senna obtusifolia* seed powder; and the *Senna obtusifolia* seed powder is extracted with the 40-85% ethanol at 20-70° C. for 0.5-4 hours and 1-3 times.

In another embodiment, in the step (3), ethanol in the extract solution is removed by rotary evaporation at 60-80° C. under a vacuum of 0.06-0.095 Mpa, and the concentrated extract solution has a solid content of 10-40%.

In another embodiment, in the step (4), an amount of the membrane filtered water is 15-40 times of an amount of the residue; the residue is extracted with the membrane filtered water at 60-100° C. for 0.5-3 hours and 1-2 times; and the centrifugation is conducted at 2000-5000 r/min.

In another embodiment, in the step (4), the amount of the membrane filtered water is 25 times of the amount of the residue; the residue is extracted with the membrane filtered water at 90° C. for 2 hours and 1 time; and the centrifugation is conducted at 3000 r/min.

In another embodiment, in the step (5), the two-phase aqueous system has an ammonium sulfate concentration of 15-25% and an ethanol concentration of 25-35%.

In another embodiment, in the step (5), the two-phase aqueous system has an ammonium sulfate concentration of 23% and an ethanol concentration of 30%.

In another embodiment, in the step (6), the bottom layer is filtered through a 200-500 mesh filter cloth and an ultrafiltration membrane with a molecular weight cut-off of 100 k.

In another embodiment, in the step (3), the *Senna obtusifolia* seed extract has an anthraquinone content of more than 4%.

In another embodiment, in the step (6), the galactomannan extract has a galactomannan content of more than 80%.

The present invention provides a process technology for comprehensive utilization of *Senna obtusifolia* seeds, the obtained *Senna obtusifolia* seed extract has a content of anthraquinone of more than 4%, and the process of obtaining *Senna obtusifolia* seed by using two-phase extraction technology is simple and feasible, and is suitable for industrial production.

DETAILED DESCRIPTION

Example 1

Taking 1 kg of dried *Senna obtusifolia* seeds, crushing to make coarse powder, passing through 20 mesh sieve, adding 6 kg of 70% ethanol, extracting at 60° C. for 2 times, 1 hour each time, filtering to obtain an extract solution and a *Senna obtusifolia* seed residue, recovering ethanol under reduced pressure to obtain a concentrated extract solution with a solid content of 25%. The concentrated extract solution was directly spray dried to obtain 142 g of *Senna obtusifolia* seed extract with a total anthraquinone content of 5.3%. The *Senna obtusifolia* seed residue was added with 25 times amount of membrane filtered water and extracted for 2 hours at 95° C. A supernatant was obtained by centrifuging the mixture of the residue and water at 3000 r/min. The supernatant was added with ammonium sulfate to reach a concentration of ammonium sulfate of 23%, and ethanol was added to a volume fraction of 30% to form a two-phase aqueous system. The two-phase aqueous system was stirred evenly, and stood still for phase separation. Galactomannan was distributed in the lower phase. The lower phase was collected and filtered through a 300-mesh filter cloth and an ultrafiltration membrane with a cut-off molecular weight of 100 k to remove small molecules and salt impurities to obtain a galactomannan extract solution. The galactomannan extract solution was vacuum dried to obtain a galactomannan extract, with a yield of 12.3% and a galactomannan content of 84%.

Example 2

Taking 1 kg of dried *Senna obtusifolia* seeds, crushing to make coarse powder, passing through 20 mesh sieve, adding 6 kg of 20% ethanol, extracting at 60° C. for 2 times, 1 hour each time, filtering to obtain an extract solution and a *Senna obtusifolia* seed residue, recovering ethanol under reduced pressure to obtain a concentrated extract solution with a solid content of 25%. The concentrated extract solution was directly spray dried to obtain 189 g of *Senna obtusifolia* seed extract with a total anthraquinone content of 0.7%. The *Senna obtusifolia* seed residue was added with 25 times amount of membrane filtered water and extracted for 2 hours at 95° C. A supernatant was obtained by centrifuging the mixture of the residue and water at 3000 r/min. The supernatant was added with ammonium sulfate to reach a concentration of ammonium sulfate of 23%, and ethanol was added to a volume fraction of 30% to form a two-phase aqueous system. The two-phase aqueous system was stirred evenly, and stood still for phase separation. Galactomannan was distributed in the lower phase. The lower phase was collected and filtered through a 300-mesh filter cloth and an ultrafiltration membrane with a cut-off molecular weight of 100 k to remove small molecules and salt impurities to obtain a galactomannan extract solution. The galactomannan extract solution was vacuum dried to obtain a galactomannan extract, with a yield of 9.7% and a galactomannan content of 56%.

Example 3

Taking 1 kg of dried *Senna obtusifolia* seeds, crushing to make coarse powder, passing through 20 mesh sieve, adding 6 kg of 70% ethanol, extracting at 60° C. for 2 times, 1 hour each time, filtering to obtain an extract solution and a *Senna obtusifolia* seed residue, recovering ethanol under reduced pressure to obtain a concentrated extract solution with a solid content of 25%. The concentrated extract solution was directly spray dried to obtain 142 g of *Senna obtusifolia* seed extract with a total anthraquinone content of 5.3%. The *Senna obtusifolia* seed residue was added with 25 times amount of membrane filtered water and extracted for 2 hours at 95° C. A supernatant was obtained by centrifuging the mixture of the residue and water at 3000 r/min. The supernatant was added with ammonium sulfate to reach a concentration of ammonium sulfate of 25%, and ethanol was added to a volume fraction of 25% to form a two-phase aqueous system. The two-phase aqueous system was stirred evenly, and stood still for phase separation. Galactomannan was distributed in the lower phase. The lower phase was collected and filtered through a 300-mesh filter cloth and an ultrafiltration membrane with a cut-off molecular weight of 100 k to remove small molecules and salt impurities to obtain a galactomannan extract solution. The galactomannan extract solution was vacuum dried to obtain a galactomannan extract, with a yield of 13.7% and a galactomannan content of 75%.

Finally, it should be noted that: obviously, the above-mentioned embodiments are merely examples for clearly illustrating the present invention, rather than limiting the implementation manners. For those of ordinary skill in the art, other changes or changes in different forms can be made on the basis of the above description. There is no need and cannot give an exhaustive list of all implementation methods. The obvious changes or changes derived from this are still within the protection scope of the present invention.

The invention claimed is:
1. A method of preparing a *Senna obtusifolia* seed extract rich in anthraquinones and a galactomannan extract, comprising the following steps sequentially:
    (1) crushing *Senna obtusifolia* seeds into a *Senna obtusifolia* seed powder;
    (2) extracting the *Senna obtusifolia* seed powder with 40-85% aqueous ethanol solution, filtering to obtain an extract solution and a residue;
    (3) concentrating the extract solution under vacuum to obtain a concentrated extract solution, spray-drying the concentrated extract solution to obtain the *Senna obtusifolia* seed extract;
    (4) extracting the residue with membrane filtered water, conducting a centrifugation to obtain a supernatant;
    (5) adding ammonium sulfate and ethanol to the supernatant to form a two-phase aqueous system, collecting a bottom layer of the two-phase aqueous system; and
    (6) conducting an ultrafiltration of the bottom layer with a cut-off molecular weight of 50 k-200 k to obtain a galactomannan extract solution, drying the galactomannan extract solution under vacuum to obtain the galactomannan extract.
2. The method of claim 1, wherein in the step (1), the *Senna obtusifolia* seed powder has a particle size of 20-60 mesh.
3. The method of claim 1, wherein in the step (2), an amount of the 40-85% aqueous ethanol solution is 3-15 times of an amount of the *Senna obtusifolia* seed powder; and the *Senna obtusifolia* seed powder is extracted with the 40-85% aqueous ethanol solution at 20-70° C. for 0.5-4 hours and 1-3 times.
4. The method of claim 1, wherein in the step (3), ethanol in the extract solution is removed by rotary evaporation at 60-80° C. under a vacuum of 0.06-0.095 Mpa, and the concentrated extract solution has a solid content of 10-40%.
5. The method of claim 1, wherein in the step (4), an amount of the membrane filtered water is 15-40 times of an amount of the residue; the residue is extracted with the membrane filtered water at 60-100° C. for 0.5-3 hours and 1-2 times; and the centrifugation is conducted at 2000-5000 r/min.
6. The method of claim 5, wherein in the step (4), the amount of the membrane filtered water is 25 times of the amount of the residue; the residue is extracted with the membrane filtered water at 90° C. for 2 hours and 1 time; and the centrifugation is conducted at 3000 r/min.
7. The method of claim 1, wherein in the step (5), the two-phase aqueous system has an ammonium sulfate concentration of 15-25% and an ethanol concentration of 25-35%.
8. The method of claim 7, wherein in the step (5), the two-phase aqueous system has an ammonium sulfate concentration of 23% and an ethanol concentration of 30%.
9. The method of claim 1, wherein in the step (3), the *Senna obtusifolia* seed extract has an anthraquinone content of more than 4%.

10. The method of claim 1, wherein in the step (6), the galactomannan extract has a galactomannan content of more than 80%.

\* \* \* \* \*